(12) United States Patent
Chen

(10) Patent No.: US 7,828,768 B2
(45) Date of Patent: Nov. 9, 2010

(54) DISPOSABLE SYRINGE AFTER ONE TIME USAGE

(75) Inventor: Chung-Jen Chen, Tainan County (TW)

(73) Assignee: Southern Taiwan University, Tainan County (TW)

( * ) Notice: Subject to any disclaimer, the term of this patent is extended or adjusted under 35 U.S.C. 154(b) by 209 days.

(21) Appl. No.: 12/099,982

(22) Filed: Apr. 9, 2008

(65) Prior Publication Data

US 2009/0259193 A1 Oct. 15, 2009

(51) Int. Cl.
*A61M 5/00* (2006.01)

(52) U.S. Cl. ........................................ 604/110; 604/198

(58) Field of Classification Search .................. 604/110, 604/111, 187, 192, 198, 218, 164.05, 197, 604/200, 220

See application file for complete search history.

(56) References Cited

U.S. PATENT DOCUMENTS 5,057,079 A * 10/1991 Tiemann et al. ............. 604/110

\* cited by examiner

*Primary Examiner*—Kevin C. Sirmons
*Assistant Examiner*—Kami A Bosworth
(74) *Attorney, Agent, or Firm*—Rosenberg, Klein & Lee

(57) ABSTRACT

A disposable syringe after one time usage includes an outer tube having an inner teeth set formed on the inner wall of the outer tube and an inner tube having an outer teeth set formed on the outer wall of the inner tube and a safety guide. The inner teeth set of the outer tube meshes with the outer teeth set of the inner tube. The single direction design of the teeth sets allows the outer tube to be pulled away from the inner tube, but not to be pushed back. The pulling force of the outer tube will pull the safety guide to form a damaged groove and the outer tube is adapted to enclose a needle so that the needle is not exposed outwardly, which prevents the needle from poking people accidentally. The syringe is unable to be reused.

2 Claims, 8 Drawing Sheets

DISPOSABLE SYRINGE AFTER ONE TIME USAGE

BACKGROUND OF THE INVENTION

1. Field of the Invention

The present invention relates to a disposable syringe after one time usage, and more particularly to a syringe with safety design to prevent the syringe from being reused as well as to be poked accidentally.

2. Description of the Prior Art

A conventional disposable syringe, as taught in Taiwanese Published No. 492329, uses too many parts, causing a higher cost of manufacture. Hence, it is not in favor by hospitals. Other than that, when operating the syringe, a person must take special training and practices before he/she can handle it properly. There are three types of safety syringes on the market, all of which are traditional syringes with self destroyable features.

FIG. 6 shows a first conventional syringe. After the injection is completed, a push rod C is pushed to meet a needle B at the end of the syringe. By pulling the push rod C back, the needle B is retreated with the push rod C into a tube A. By breaking the push rod C, the needle B is left in the tube A for safety reason.

FIG. 7 shows a second conventional syringe, which discloses a spiral push rod safety syringe. After the injection, the push rod C is turned to 30 degrees so that the push rod C is connected with the needle B. By pulling the push rod C, the needle B is brought back and destroyed in the tube A.

FIG. 8 shows a third conventional syringe, which comprises a ring sleeve D on the tube A. By turning the ring sleeve D, the push rod C is connected with the needle B1, and then the push rod C is pulled to bring the needle B1 into the tube A. The push rod C is broken to keep the needle B1 in the tube A.

There are some shortcomings of the prior art:

1. Too many parts are adapted, that increases the cost of manufacture;

2. The operations are complicated.

SUMMARY OF THE INVENTION

According to the present invention, there is provided a disposable syringe after one time usage comprising:

an outer tube having a hollow body with a first opening and a second opening at respective ends thereof, said first opening being provided with a lip, an inner teeth set being provided on an inner wall of said outer tube;

an inner tube having a hollow body with a first opening and a second opening at respective ends thereof, said second opening being provided with a lip, an outer teeth set corresponding to said inner teeth set of said outer tube being provided on an outer wall of said inner tube, said inner tube further comprising a safety guide on the outer wall and a connecting block close to said second opening of said inner tube, said connecting block being connected to the inner wall of said outer tube, and a piston rod inserted into said inner tube, said piston rod having a piston near said first opening of said inner tube.

Preferably, said inner teeth set of said outer tube and said outer teeth set of said inner tube are formed with one-way teeth.

Preferably, said first opening of said inner tube is provided with a needle seat having a needle thereon.

It is the primary object of the present invention to provide a disposable syringe after one time usage, which uses less parts and is cost-effective.

It is another object of the present invention to provide a disposable syringe after one time usage, which is easy to operate without any special skill or training.

It is a further object of the present invention to provide a disposable syringe after one time usage, which is safe in use.

It is still a further object of the present invention to provide a disposable syringe after one time usage, which prevents the syringe from a second use.

It is still a further object of the present invention to provide a disposable syringe after one time usage, which uses a single method to produce a safety and one time usage syringe.

DETAILED DESCRIPTION OF THE PREFERRED EMBODIMENT

Figure 1:
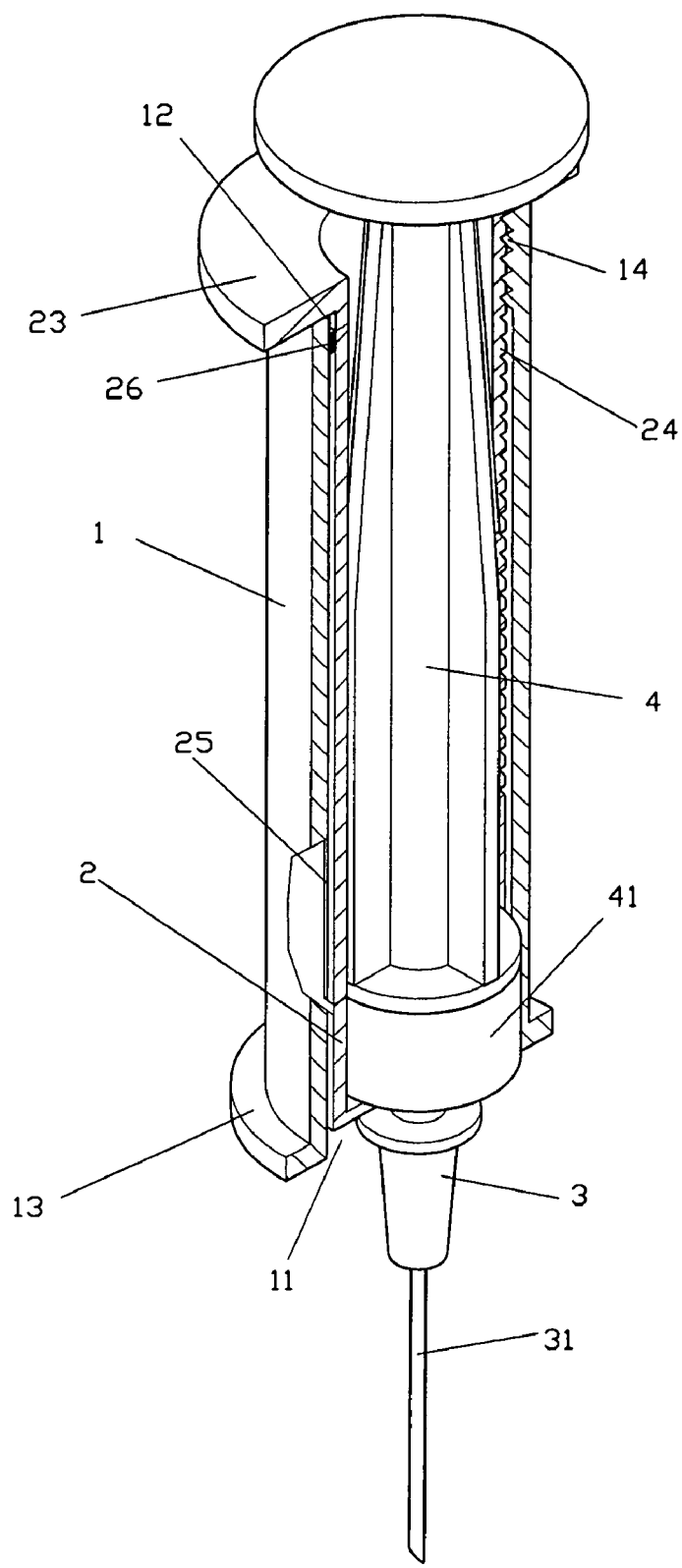
FIG. 1 is a perspective view of the present invention, partially sectioned.
Figure 2:
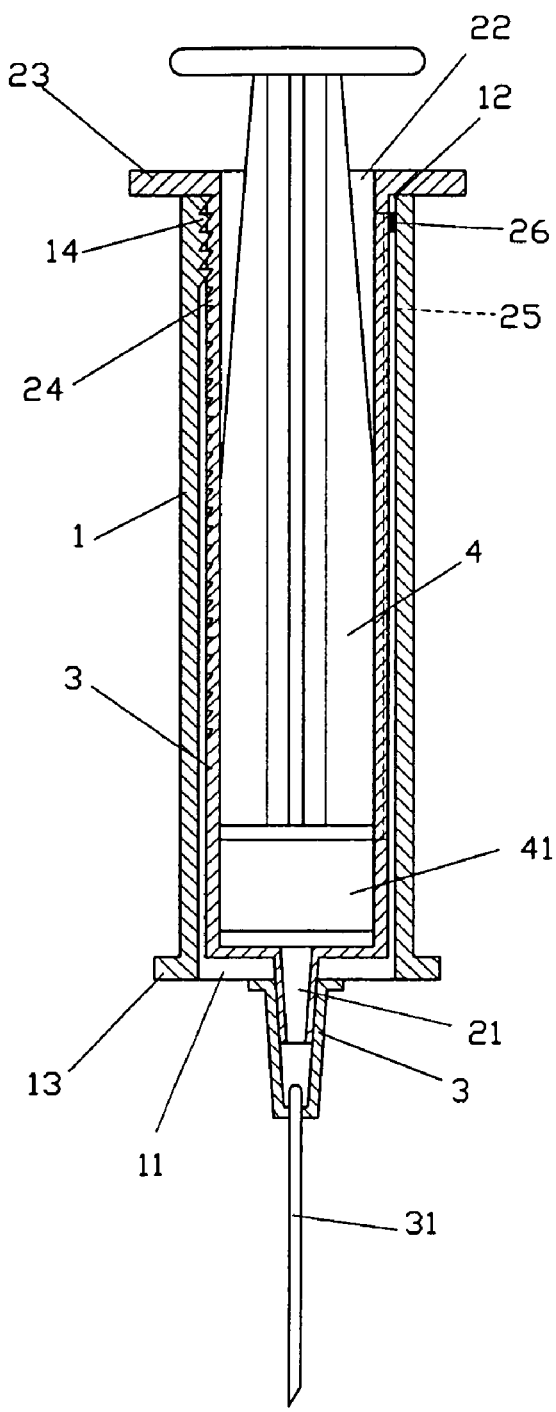
FIG. 2 is a cross-sectional view of the present invention.
Figure 3:
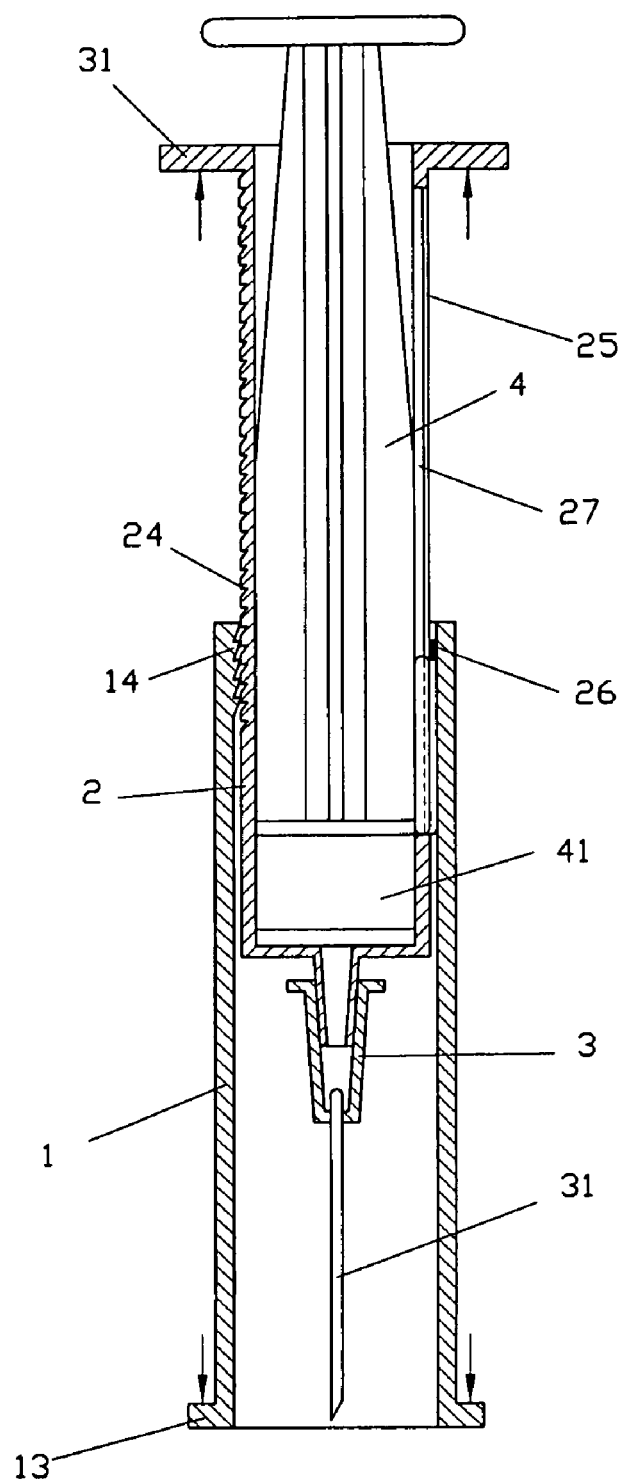
FIG. 3 is a cross-sectional view showing an outer tube being pulled away from an inner tube of the syringe of present invention.

As shown in FIGS. 1 through 3, a preferred embodiment of the present invention comprises an outer tube 1, an inner tube 2, a needle seat 3, and a piston rod 4.

The outer tube 1 has a hollow body with a first opening 11 and a second opening 12 at respective ends thereof. The first opening 11 is provided with a lip 13, and the inner wall of the outer tube 1 is provided with an inner teeth set 14.

The inner tube 2 has a hollow body with a first opening 21 and a second opening 22 at respective ends thereof. The second opening 22 is provided with a lip 23, and the outer wall of the inner tube 2 is provided with an outer teeth set 24 corresponding to the inner teeth set 14 of the outer tube 1. The inner tube 2 further comprises a safety guide 25 on the outer wall and a connecting block 26 close to the second opening 22. The connecting block 26 is connected to the inner wall of the outer tube 1.

The needle seat 3 is provided with a needle 31.

The piston rod 4 is inserted into the inner tube 2, and comprises a piston 41 at one end near the first opening 21 of the inner tube 2.

Both the inner teeth set 14 of the outer tube 1 and the outer teeth set 24 of the inner tube 2 are formed with one-way teeth.

This syringe of the present invention has changed the outer tube of a traditional syringe into an inner tube 2 with an additional outer tube 1 sleeved thereon.

The inner teeth set 14 of the outer tube 1 and the outer teeth set 24 of the inner tube 2 are meshed together. The first opening 21 of the inner tube 2 is coupled with the needle seat 3 having the needle 31 thereon. The piston rod 4 with the piston 41 is inserted into the inner tube 2, and the safety guide 25 is provided on the outer wall of the inner tube 2.

The outer tube 1 has the lip 13 and the inner tube 2 has the lip 23. Both the lips 13 and 23 are adapted for easy operation of the tubes 1 and 2, which is a traditional skill, thus it will not be described hereinafter.

To operate the syringe of the present invention, the needle 31 is poked into a medical bottle and the piston rod 4 is pulled back to draw medicine from the bottle into the inner tube 2, the needle 31 is pulled out from the bottle and poked again on the patient, and the piston rod 4 is pushed to inject medicine into the patient.

Figure 4:
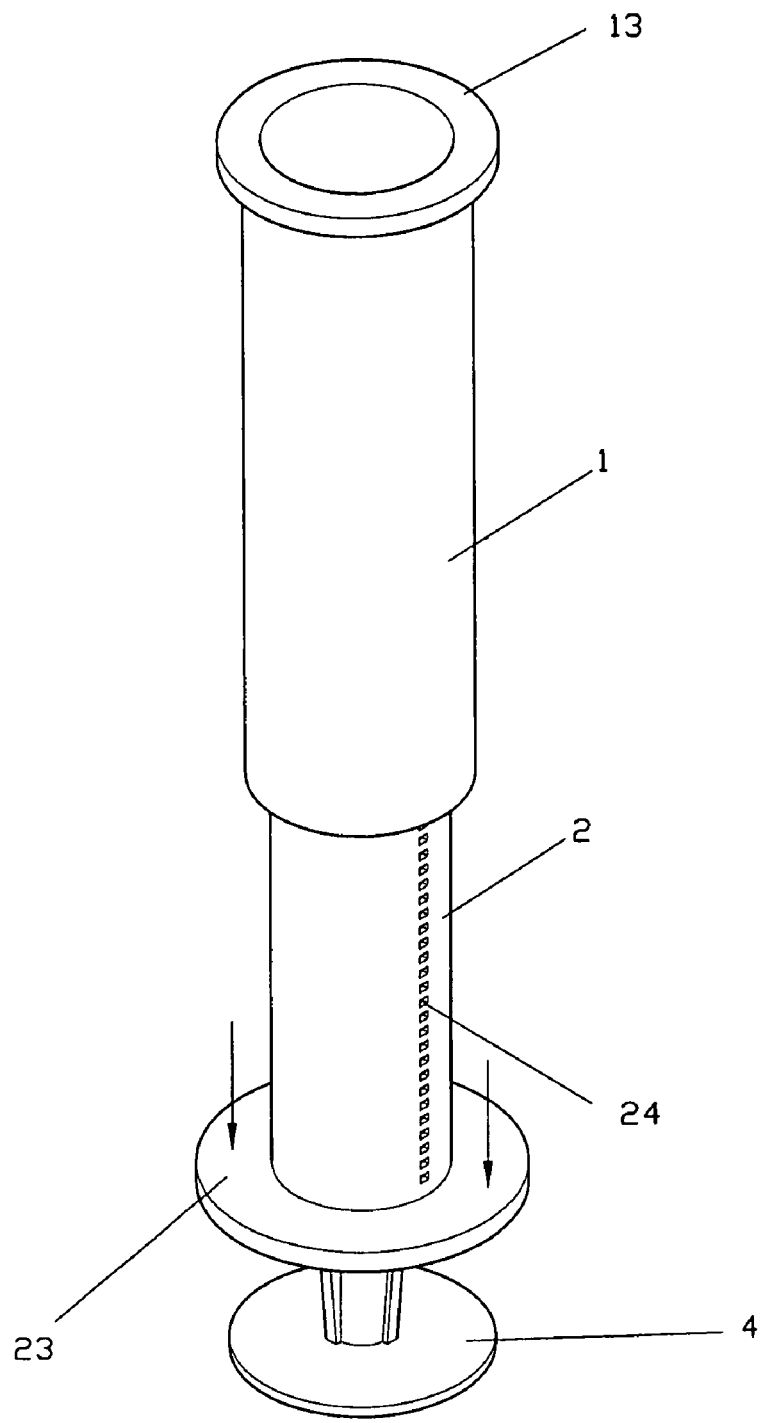
FIG. 4 is a perspective view of FIG. 3.

As shown in FIGS. 3 and 4, the inner teeth set 14 of the outer tube 1 and the outer teeth set 24 of the inner tube 2 are provided with one-way teeth so that the outer tube 1 is unable to be pushed back when the outer tube 1 is pulled away from the inner tube 2.

After injection, the lip 13 of the outer tube 1 and the lip 23 of the inner tube 2 are pulled toward an opposite direction (the arrow indicates the forcing direction), which brings the outer tube 1 and the inner tube 2 to move toward opposite directions. The piston rod 4 and the needle 31 of the needle seat 3 are linked to move and the needle 31 is drawn back inside the outer tube 1 so as to prevent the needle 31 from poking accidentally.

Figure 5:
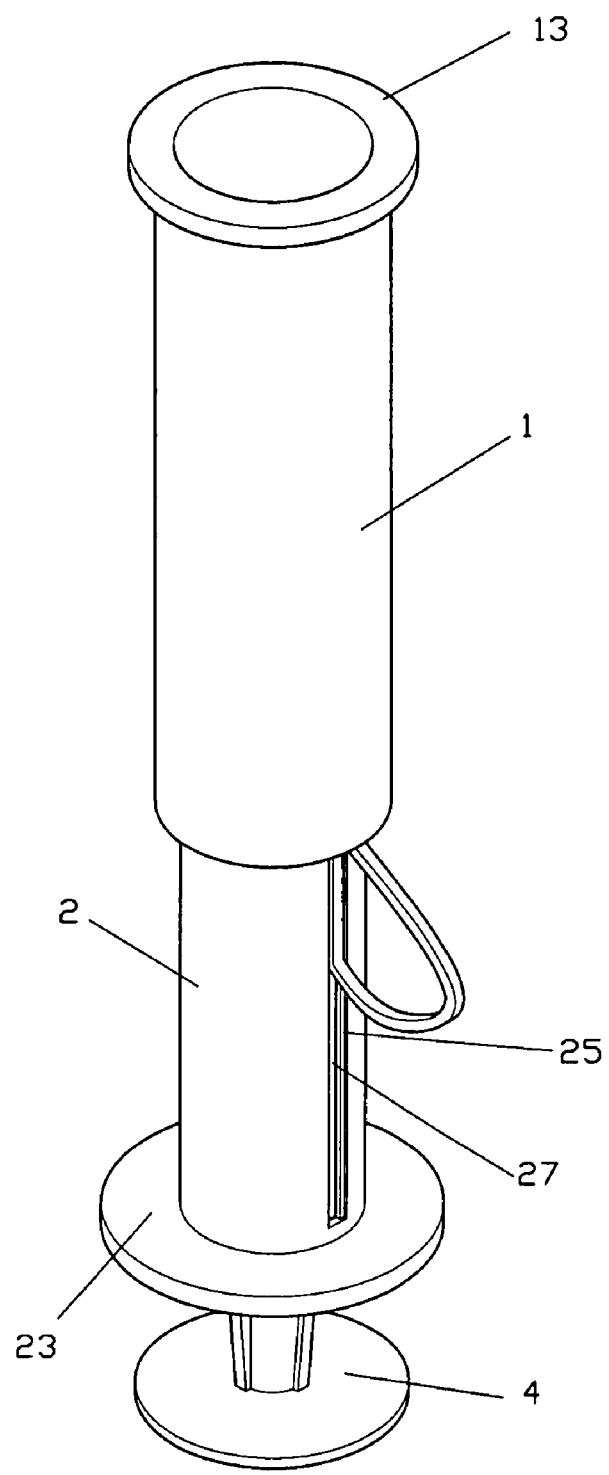
FIG. 5 is a perspective view of the present invention showing a safety guide being pulled to form a damaged groove.
Figure 6:
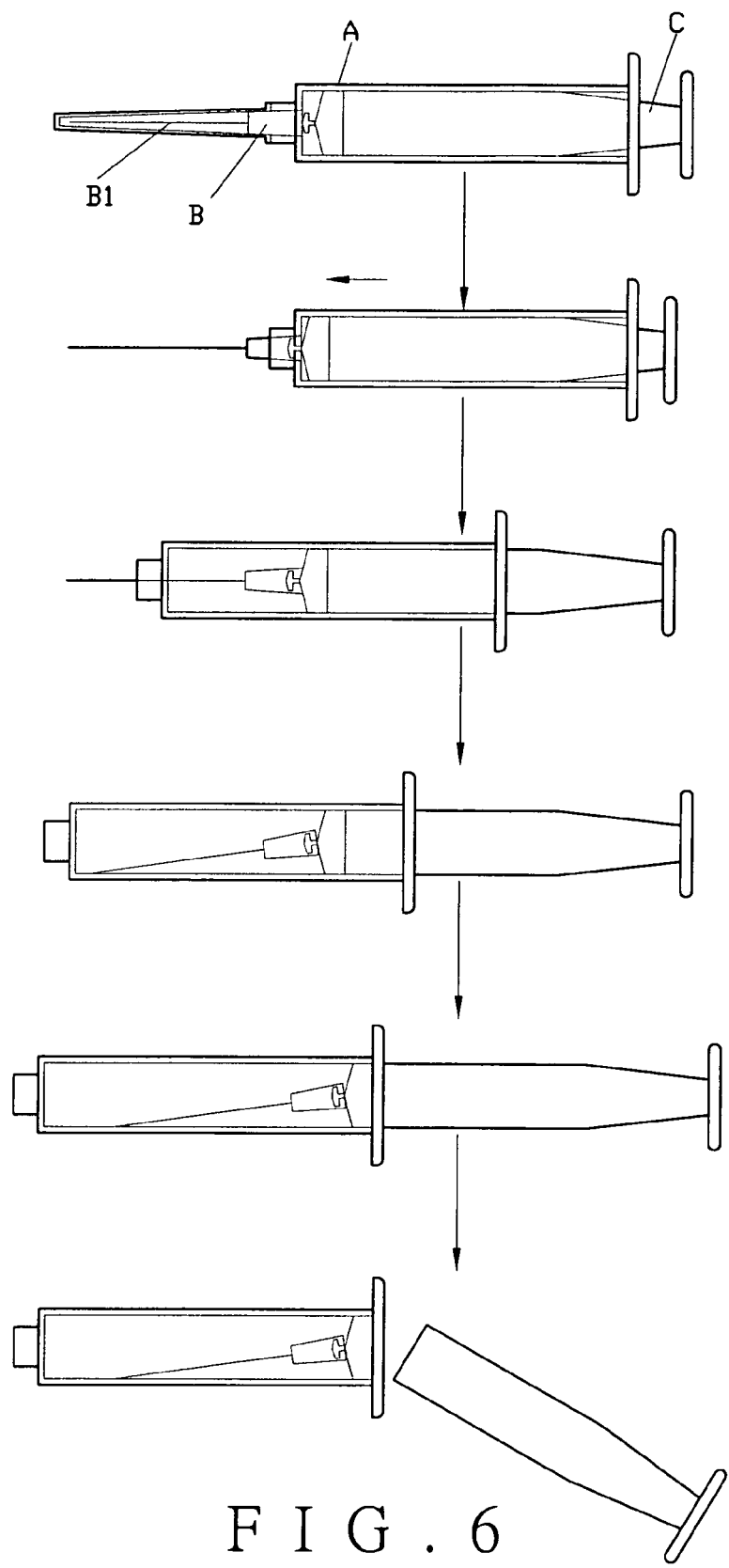
FIG. 6 is a diagram showing a first conventional syringe.
Figure 7:
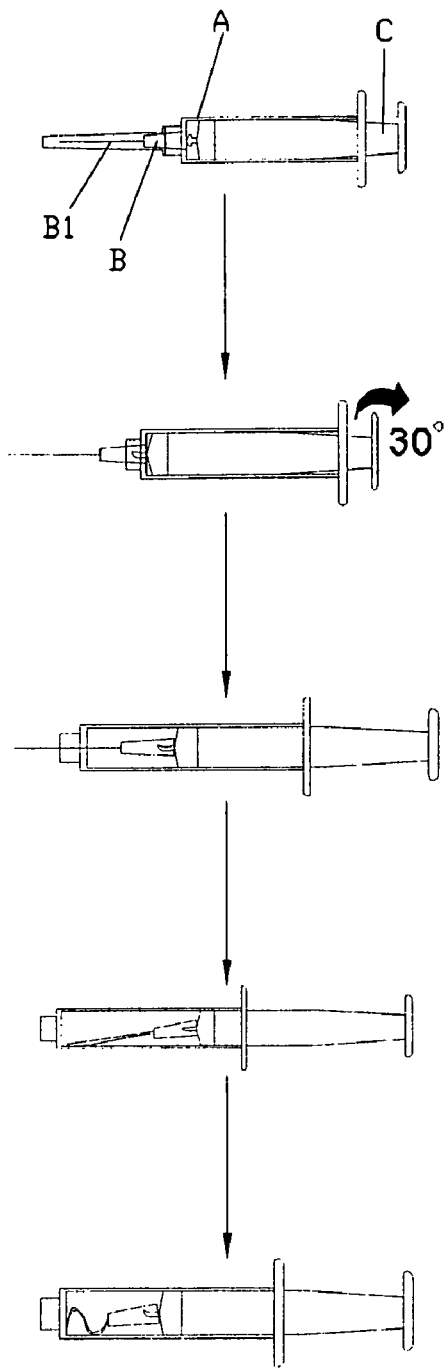
FIG. 7 is a diagram showing a second conventional syringe.
Figure 8:
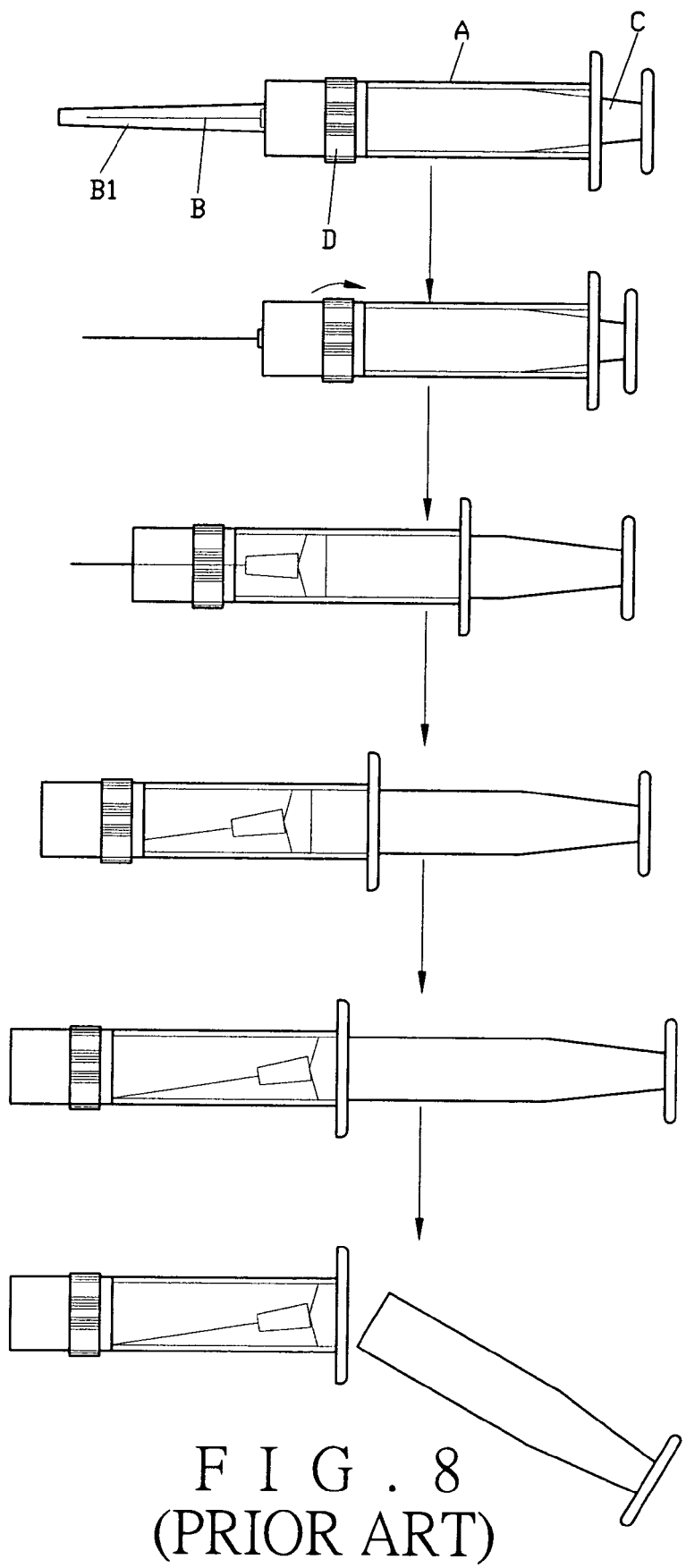
FIG. 8 is a diagram showing a third conventional syringe.

When the outer tube 1 is pulled away from the inner tube 2, the safety guide 25 on the outer wall of the inner tube 2 will be pulled away from the inner tube 2 to form a damaged groove 27 on the inner tube 2, as shown in FIG. 5. The pulled away portion of the safety guide 25 and the one-way teeth of the teeth sets 14 and 24 restrict the inner tube 2 from being pushed back toward the bottom of the outer tube 1.

The safety guide 25 of the inner tube 2 will be pulled away from the inner tube 2 when the outer tube 1 is moved relative to the inner tube 2, as shown in FIG. 5. The pulled away portion of the safety guide 25 restrains the syringe from being reused.

According to the aforesaid, it is understood that this design providing a disposable syringe after one time usage has added an extra outer tube having an inner teeth set and an inner tube having an outer teeth set. This design is to use the teeth sets to restrain the syringe from being reused.

What is claimed is:

1. A disposable syringe after one time usage comprising:
   an outer tube having a hollow body with a first opening and a second opening at respective ends thereof, said first opening being provided with a lip, an inner teeth set being provided on an inner wall of said outer tube;
   an inner tube having a hollow body with a first opening and a second opening at respective ends thereof, said second opening being provided with a lip, said outer tube being telescopically sleeved over said inner tube, said inner tube having an outer teeth set formed on an outer wall thereof in correspondence with said inner teeth set of said outer tube and being engaged therewith for unidirectional displacement of one with respect to the other;
   a safety guide formed on the outer wall of said inner tube and having a connecting block disposed adjacent to said second opening of said inner tube, said connecting block being connected to the inner wall of said outer tube, whereby said unidirectional displacement of one of said inner tube and outer tube relative to the other pulls away a portion of said safety guide from said outer wall of said inner tube to form a damage groove therein, said pulled away portion of said safety guide together with said engaged inner and outer teeth sets resists reversal of said relative displacement between said inner and outer tubes; and
   a piston rod inserted into said inner tube, said piston rod having a piston near said first opening of said inner tube.

2. The disposable syringe after one time usage, as recited in claim 1, wherein said first opening of said inner tube is provided with a needle seat having a needle thereon, said relative displacement between said inner and outer tubes positioning said outer tube in telescopically sleeved relationship with said needle.

* * * * *